US010772902B2

(12) United States Patent
Prithiviraj et al.

(10) Patent No.: US 10,772,902 B2
(45) Date of Patent: Sep. 15, 2020

(54) USE OF FLORIDOSIDE OR ISETHIONIC ACID TO POTENTIATE ANTIMICROBIAL ACTIVITY OF ANTIBIOTICS

(71) Applicant: OCELAND BIOLOGICALS LIMITED, Bible Hill (CA)

(72) Inventors: Balakrishnan Prithiviraj, Bible Hill (CA); Garima Kulshrestha, Bible Hill (CA)

(73) Assignee: OCELAND BIOLOGICALS LIMITED, Bible Hill (CA)

( * ) Notice: Subject to any disclaimer, the term of this patent is extended or adjusted under 35 U.S.C. 154(b) by 5 days.

(21) Appl. No.: 16/074,554

(22) PCT Filed: Jan. 27, 2017

(86) PCT No.: PCT/CA2017/050091
§ 371 (c)(1),
(2) Date: Aug. 1, 2018

(87) PCT Pub. No.: WO2017/132755
PCT Pub. Date: Aug. 10, 2017

(65) Prior Publication Data
US 2019/0038651 A1 Feb. 7, 2019

Related U.S. Application Data

(60) Provisional application No. 62/290,802, filed on Feb. 3, 2016.

(51) Int. Cl.
| | | |
|---|---|---|
| *A61K 31/7032* | (2006.01) | |
| *C07H 15/04* | (2006.01) | |
| *A61K 31/185* | (2006.01) | |
| *A61K 45/06* | (2006.01) | |
| *A61P 31/04* | (2006.01) | |
| *A61K 31/65* | (2006.01) | |

(52) U.S. Cl.
CPC ........ *A61K 31/7032* (2013.01); *A61K 31/185* (2013.01); *A61K 31/65* (2013.01); *A61K 45/06* (2013.01); *A61P 31/04* (2018.01); *C07H 15/04* (2013.01); *Y02A 50/481* (2018.01)

(58) Field of Classification Search
None
See application file for complete search history.

(56) References Cited

U.S. PATENT DOCUMENTS

| | | |
|---|---|---|
| 5,556,577 A | 9/1996 | Gomes et al. |
| 5,891,835 A | 4/1999 | Vlasblom |
| 5,942,478 A | 8/1999 | Lopes |
| 8,946,436 B2 | 2/2015 | Luo et al. |
| 2005/0222163 A1 | 10/2005 | Eck et al. |
| 2015/0374786 A1* | 12/2015 | Bochner ............... A61K 38/05 514/2.4 |

FOREIGN PATENT DOCUMENTS

| | | | |
|---|---|---|---|
| KR | 100777780 B1 * | 11/2007 | ............. A01N 65/00 |
| KR | 100777780 B1 | 11/2007 | |

OTHER PUBLICATIONS

Chopra et al., "Tetracycline Antibiotics: Mode of Action, Applications, Molecular Biology, and Epidemiology of Bacterial Resistance," Microbiology and Molecular Biology Reviews, Jun. 2001, vol. 65 (2), pp. 232-260. XP002346522.
European Patent Application No. 17746665.3, Extended European Search Report dated Oct. 16, 2019.
Hellio et al., "Isethionic Acid and Floridoside Isolated From the Red Alga, Grateloupia Turuturu, Inhibit Settlement of Balanus Amphitrite Cyprid Larvae," Biofouling, Jun. 2004, vol. 20 (3), pp. 139-145.
Husain et al., "Quorum Sensing Inhibitors From Natural Products as Potential Novel Anti-Infective Agents," Drugs of the Future, Oct. 2013, vol. 38 (10), pp. 691-706. XP055629333.
International Patent Application No. PCT/CA2017/050091, International Preliminary Report on Patentability dated Aug. 16, 2018.
International Patent Application No. PCT/CA2017/050091, International Search Report and Written Opinion dated Apr. 25, 2017.
Kalia., "Quorum Sensing Inhibitors: An Overview," Biotechnology Advances, Mar.-Apr. 2013, vol. 31 (2), pp. 224-245. XP055467924.
Kerjean et al., "Optimization of Floridoside Production in the Red Alga Mastocarpus Stellatus: Pre-Conditioning, Extraction and Seasonal Variations," Botanica Marina, Apr. 2007, vol. 50 (1), pp. 59-64.
Kulshreshtha., "The Use of Selected Red Macroalgae (Seaweeds) for the Reduction of *Salmonella enteritidis* in Poultry," Thesis—Dalhousie University, Feb. 2016, 211 pages.
Liu et al., "The Effects of Betonicine, Floridoside and Isethionic Acid from the Red Alga Ahnfeltiopsis Flabelliformis on Quorum-Sensing Activity," Biotechnology and Bioprocess Engineering, Aug. 2008, vol. 13 (4), pp. 458-463. XP055404777.
Richards et al., "Enhancement of Antibacterial Activity by p-aminobenzoic Acid and Sulphadiazine," International Journal of Pharmaceutics, Apr. 1992, vol. 82 (1-2), pp. 107-115. XP025557791.
Simon-Colin et al., "Characterization of N-Methyl-L-Methionine Sulfoxide and Isethionic Acid From the Red Alga Grateloupia Doryphora," Phycological Research, Jun. 2002, vol. 50 (2), pp. 125-128.

* cited by examiner

*Primary Examiner* — Dale R Miller
(74) *Attorney, Agent, or Firm* — Borden Ladner Gervais LLP; David Nauman

(57) ABSTRACT

The present disclosure provides: floridoside or isethionic acid for use as an antibiotic potentiator; floridoside or isethionic acid in a combination therapy with an antibiotic compound; as well as methods of potentiating the antibiotic activity of an antibiotic compound, where the method comprises administering floridoside or isethionic acid to an animal or plant.

17 Claims, 8 Drawing Sheets
Specification includes a Sequence Listing.

SEQUENCE LISTING

```
<160> NUMBER OF SEQ ID NOS: 6

<210> SEQ ID NO 1
<211> LENGTH: 23
<212> TYPE: DNA
<213> ORGANISM: Artificial Sequence
<220> FEATURE:
<223> OTHER INFORMATION: Synthetic construct

<400> SEQUENCE: 1
cgtcatgcgg ggtattccaa gtg                                             23

<210> SEQ ID NO 2
<211> LENGTH: 18
<212> TYPE: DNA
<213> ORGANISM: Artificial Sequence
<220> FEATURE:
<223> OTHER INFORMATION: Synthetic construct

<400> SEQUENCE: 2
cgcgccgcca gttttagc                                                   18
```

```
<210> SEQ ID NO 3
<211> LENGTH: 20
<212> TYPE: DNA
<213> ORGANISM: Artificial Sequence
<220> FEATURE:
<223> OTHER INFORMATION: Synthetic construct

<400> SEQUENCE: 3
atccgcagcc gtaaaatgac                                        20

<210> SEQ ID NO 4
<211> LENGTH: 20
<212> TYPE: DNA
<213> ORGANISM: Artificial Sequence
<220> FEATURE:
<223> OTHER INFORMATION: Synthetic construct

<400> SEQUENCE: 4
tggttcagcg gcagcatata                                        20

<210> SEQ ID NO 5
<211> LENGTH: 24
<212> TYPE: DNA
<213> ORGANISM: Artificial Sequence
<220> FEATURE:
<223> OTHER INFORMATION: Synthetic construct

<400> SEQUENCE: 5
ttttgcaggg cgcggtcaga atac                                   24

<210> SEQ ID NO 6
<211> LENGTH: 21
<212> TYPE: DNA
<213> ORGANISM: Artificial Sequence
<220> FEATURE:
<223> OTHER INFORMATION: Synthetic construct

<400> SEQUENCE: 6
tgcggtgccc agctcaacga t                                      21
```

USE OF FLORIDOSIDE OR ISETHIONIC ACID TO POTENTIATE ANTIMICROBIAL ACTIVITY OF ANTIBIOTICS

FIELD

The present disclosure relates to compounds that potentiate antibiotic activity, as well as methods and uses thereof.

BACKGROUND

The following paragraphs are not an admission that anything discussed in them is prior art or part of the knowledge of persons skilled in the art.

Antibiotics are used in the treatment of infectious diseases caused by bacteria in humans, animals and plants. However, the increased use of antibiotics has resulted in an increase in the number of drug resistant strains of pathogenic bacteria.

INTRODUCTION

The following introduction is intended to introduce the reader to this specification but not to define any invention. One or more inventions may reside in a combination or sub-combination of the apparatus elements or method steps described below or in other parts of this document. The inventors do not waive or disclaim their rights to any invention or inventions disclosed in this specification merely by not describing such other invention or inventions in the claims.

Although it is desirable to identify new antibiotic classes and new antibiotic molecules in order to overcome drug resistance in bacteria, it is also desirable to identify compounds that potentiate the activity of existing antibiotics. Using such potentiating compounds in combination therapies with an existing antibiotic may increase the antibiotic activity sufficiently to treat bacterial infections of otherwise drug resistant bacteria.

Therefore, it is desirable to identify compounds that potentiate the activity of one or more already existing antibiotics, and it is desirable to identify potentiating compounds that can be used in combinatorial therapies to treat bacterial infections.

Floridoside (2-O-α-D-galactopyranosylglycerol) has been identified by the authors of the present disclosure as one example of a compound that can be used to potentiate the antibiotic activity of at least one antibiotic. Floridoside may be used in combination with an antibiotic to treat a bacterial infection, where the concentration of the antibiotic necessary to treat the bacterial infection is lower than the concentration of the antibiotic necessary to achieve comparable treatment in the absence of floridoside.

Isethionic acid has been identified by the authors of the present disclosure as another example of a compound that can be used to potentiate the antibiotic activity of at least one antibiotic. Isethionic acid may be used in combination with an antibiotic to treat a bacterial infection, where the concentration of the antibiotic necessary to treat the bacterial infection is lower than the concentration of the antibiotic necessary to achieve comparable treatment in the absence of isethionic acid.

In some embodiments, the present disclosure provides floridoside for use as an antibiotic potentiator. In other embodiments, the present disclosure provides floridoside in combination with an antibiotic compound. In yet other embodiments, the present disclosure provides a method of potentiating the antibiotic activity of an antibiotic compound, where the method comprises administering floridoside along with the antibiotic compound.

In some embodiments, the present disclosure provides isethionic acid for use as an antibiotic potentiator. In other embodiments, the present disclosure provides isethionic acid in combination with an antibiotic compound. In yet other embodiments, the present disclosure provides a method of potentiating the antibiotic activity of an antibiotic compound, where the method comprises administering isethionic acid along with the antibiotic compound.

BRIEF DESCRIPTION OF THE DRAWINGS

Embodiments of the present disclosure will now be described, by way of example only, with reference to the attached Figures.

DETAILED DESCRIPTION

Figure 1:
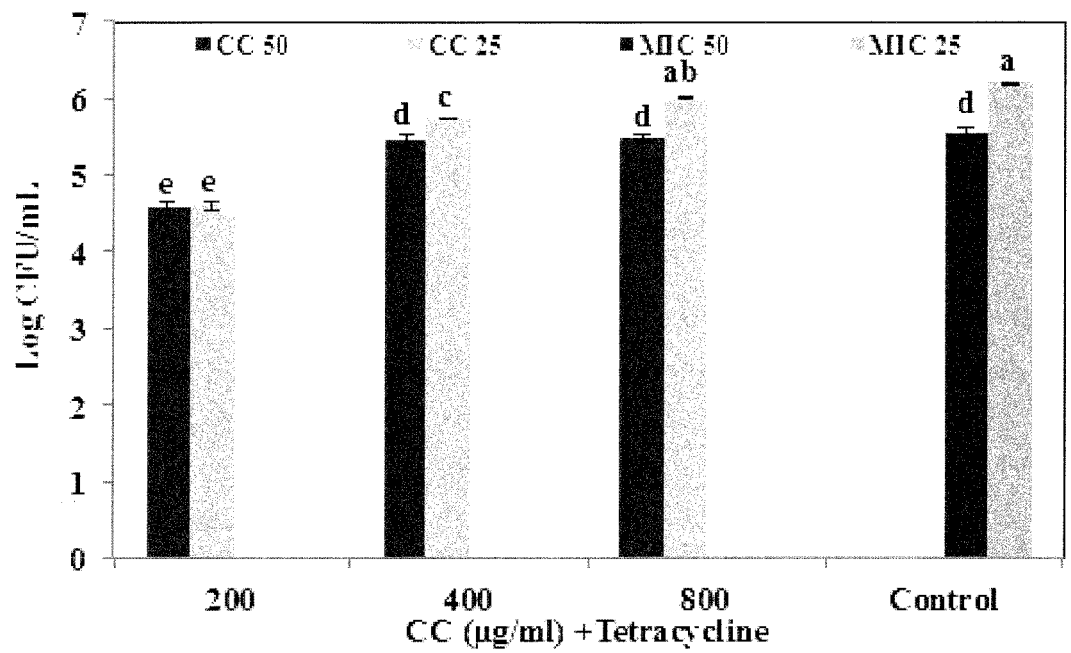
FIG. 1 is a graph illustrating the combined antibacterial effect on *S. Enteritidis* of tetracycline at $MIC_{25}$ or $MIC_{50}$ with 200, 400 or 800 µg/mL of *Chondrus crispus* extract.
Figure 2:
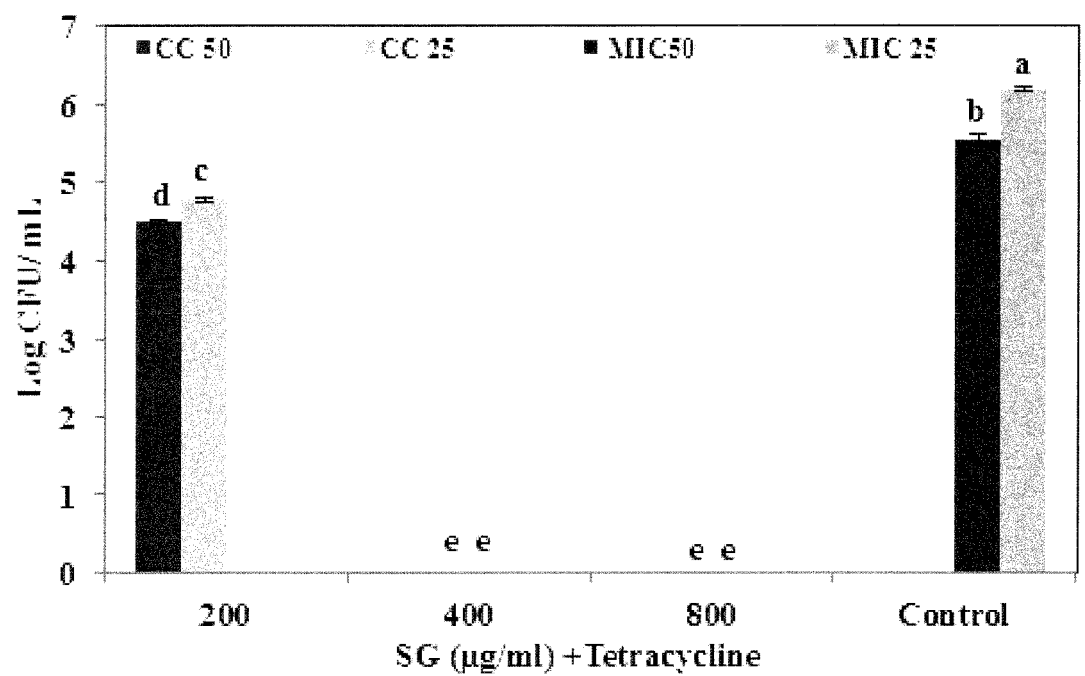
FIG. 2 is a graph illustrating the combined antibacterial effect on *S. Enteritidis* of tetracycline at $MIC_{25}$ or $MIC_{50}$ with 200, 400 or 800 µg/mL of *Sarcodiotheca gaudichaudii* extract.
Figure 3:
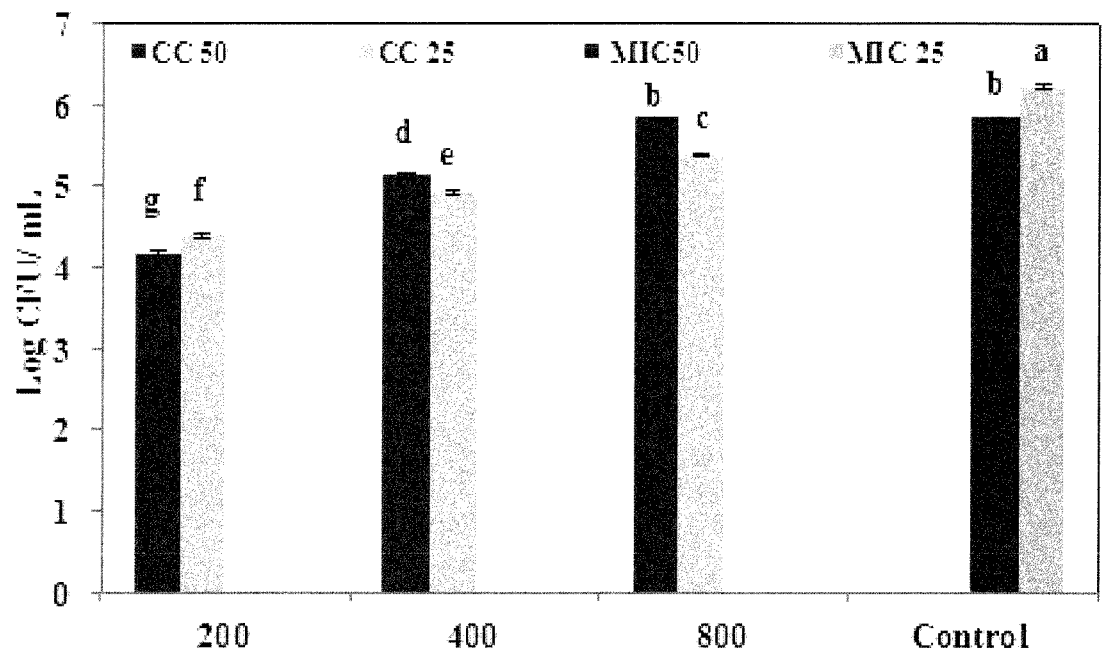
FIG. 3 is a graph illustrating the combined antibacterial effect on *S. Enteritidis* of streptomycin at $MIC_{25}$ or $MIC_{50}$ with 200, 400 or 800 µg/mL of *Chondrus crispus* extract.
Figure 4:
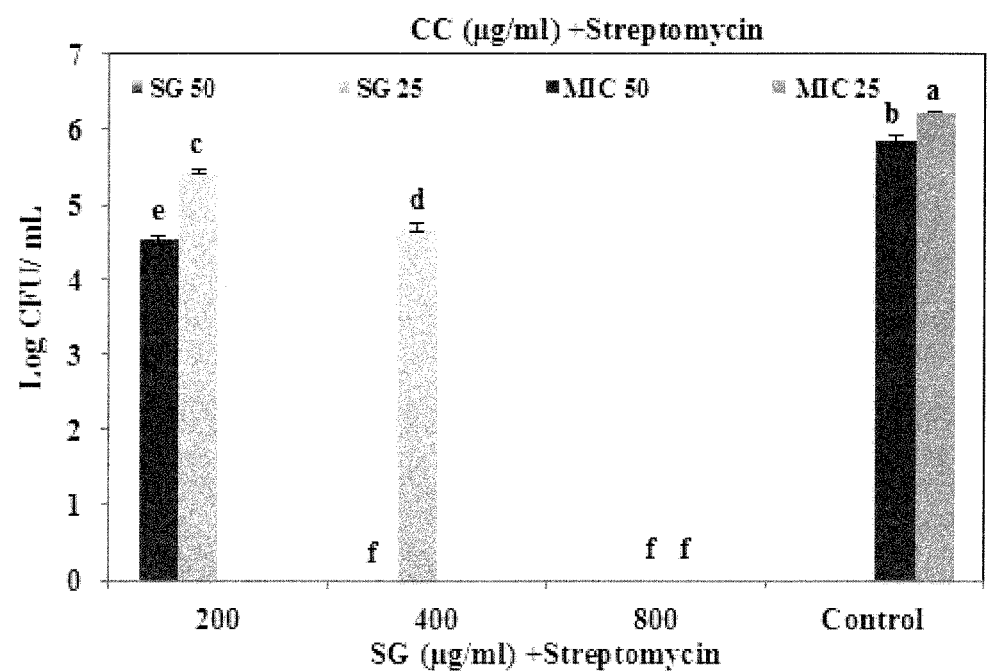
FIG. 4 is a graph illustrating the combined antibacterial effect on *S. Enteritidis* of streptomycin at $MIC_{25}$ or $MIC_{50}$ with 200, 400 or 800 µg/mL of *Chondrus crispus* extract.

Generally, the present disclosure provides: floridoside for use as an antibiotic potentiator; floridoside in combination with an antibiotic compound; as well as methods of potentiating the antibiotic activity of an antibiotic compound, where the method comprises administering floridoside along with the antibiotic compound. The present disclosure also provides isethionic acid for use as an antibiotic potentiator; isethionic acid in combination with an antibiotic compound; as well as methods of potentiating the antibiotic activity of an antibiotic compound, where the method comprises administering isethionic acid along with the antibiotic compound.

In the context of the present disclosure, "potentiate" refers to the ability of a compound to reduce the minimum inhibitory concentration (MIC) of an antibiotic in at least one bacteria, as tested in a broth inoculation method where the MIC is determined by the lowest concentration of antibiotic required for complete inhibition of the bacteria after incubation at 37° C. for 16-18 h in an incubator shaking at 200 rpm.

In some examples, a compound that is found to potentiate antibiotic activity may be used in combination with the antibiotic to treat a bacterial infection, and the concentration of the antibiotic necessary to treat the bacterial infection may be lower than the concentration of the antibiotic necessary to achieve comparable treatment in the absence of the potentiating compound.

Floridoside or isethionic acid may be used to potentiate the antibiotic activity of an antibiotic that is removed from bacteria by bacterial efflux pumps.

Efflux pumps are membrane transport proteins that use cellular energy to move a toxic substance, such as an antibiotic, from the interior of the bacterium into the external environment. Efflux pumps capable of transporting a range of structurally dissimilar compounds confer multidrug resistance (MDR) and are known as multidrug efflux pumps. Without wishing to be bound by theory, the authors of the present disclosure believe that floridoside, isethionic acid, or both, potentiate antibiotic activity by reducing the expression of one or more genes that encode efflux pumps. This reduced gene expression may be achieved by reducing transcription of the gene.

Since efflux pumps help bacteria survive by pumping out xenobiotics, including antibiotics, the authors of the present disclosure believe that reducing transcription of one or more genes that encode such efflux pumps results in an increase in concentration of the antibiotic. Reducing expression of one or more efflux related genes decreases the efficiency of the bacterium to remove the antibiotic from the cell. Thus in the presence of floridoside or isethionic acid, the bacterium accumulates antibiotic to the level which can kill the cell, for example by inhibiting protein synthesis in the cell.

In bacteria, several genes have been identified that encode multidrug efflux proteins. Multiple drug efflux system can be classified into five families based on: the number of pump components (single vs. multiple pump components), the substrate exported by pump, the number of transmembrane-spanning regions, and the source of energy used by the pump. These families include: the ATP binding cassette (ABC) family, multidrug and toxic compound exporters (MATE), the small multidrug resistance (SMR) family, resistance-nodulation-division proteins (RND), and the major facilitator superfamily (MFS). Four of these systems require proton motive force as an energy source. The ABC family utilizes ATP (hydrolysis) to mediate the substrate extrusion. Single-component transporters mediate the efflux of toxic compounds across the cytoplasmic membrane (CM). Multiple components transporters catalyze efflux across the outer membrane (OM) or across the periplasmic membrane. Proteins involved in the efflux include outer membrane channel proteins (OMP) and periplasmic membrane fusion proteins (MFP).

In some examples, floridoside may be used to potentiate the antibiotic activity of an antibiotic that is removed from bacteria by an efflux pump that includes a transporter protein encoded by acrB, a transcription activator encoded by ramA, or both. In some examples, floridoside may be used to potentiate the antibiotic activity of an antibiotic that is removed from bacteria by an efflux pump regulated by a protein encoded by marA. The efflux pump may be a member of the resistance-nodulation-cell division superfamily (RND). In particular examples, the efflux pump may be AcrAB.

Floridoside or isethionic acid may be used to potentiate the antibiotic activity on a Gram-negative bacterium, or a Gram-positive bacterium. Both Gram-negative and Gram-positive bacteria are known to acquire antibiotic resistance through the increased expression or acquired expression of one or more efflux pumps.

*Salmonella enterica* is a Gram-negative gastrointestinal bacteria that causes diseases such as gastroenteritis, inflammation, diarrhoea and life threatening systemic infections. A nalidixic acid resistant strain of *S. Enteritidis* was used in the experimental results discussed herein.

Although the present disclosure presents experimental results showing the potentiating ability of floridoside or isethionic acid with tetracycline and streptomycin, floridoside or isethionic acid may be used to potentiate the antibiotic activity of other antibiotics whose activity is affected by a bacterial efflux pump discussed above. For example, floridoside or isethionic acid may be used to potentiate the antibiotic activity of: tetracycline, chlortetracycline, oxytetracycline, demeclocycline, lymecycline, meclocycline, methacycline, minocycline, rolitetracycline, tigecycline, streptomycin, dihydrostreptomycin, framycetin, neomycin, neomycin C, paromomycin, ribostamycin, kanamycin, amikacin, arbekacin, bekanamycin, dibekacin, tobramycin, spectinomycin, hygromycin B, paromomycin, gentamicin, netilmicin, sisomicin, isepamicin, verdamicin, astromicin, or gentamycin. Floridoside or isethionic acid may be used to potentiate the antibiotic activity of a β-lactam antibiotic, such as carbenicillin, sulbenicillin, ceftazidime, moxalactam, aztreonam, fluoroquinolones, imipenem, or trimethoprim.

The floridoside, the isethionic acid, or both may be extracted, isolated, or both, from red seaweed. Examples of red seaweed that may be used to produce floridoside or isethionic acid include: *Chondrus crispus, Gymnogongrus devoniensis, Palmaria palmata Sarcodiotheca gaudichaudii, Solieria chordalis* and *Sarcodiotheca* spp. It is particularly desirable to use *Chondrus crispus* or *Sarcodiotheca gaudichaudii* to produce floridoside since these species of red seaweed have higher concentrations of floridoside than the other listed species.

Floridoside and isethionic acid may be extracted together from dried sea weed using distilled water. The dried sea weed is preferably a powder to increase the surface area of the extraction. The extraction is preferably done at an elevated temperature, such as 50° C., to increase the rate of extraction. The aqueous supernatant of the extraction may be freeze dried to concentrate the floridoside and isethionic acid.

Floridoside may be isolated from dried sea weed by extracting with a mixture of ethanol and water, such as a mixture having 80% ethanol. The dried sea weed is preferably a powder to increase the surface area of the extraction.

The extraction is preferably done at an elevated temperature, such as 80° C., to increase the rate of extraction. The mixture of ethanol and water is concentrated by evaporation, optionally re-suspended in water, and extracted with ethyl acetate. The aqueous fraction of the extraction is concentrated by evaporation, and re-suspended in a methanol and water mixture, such as a mixture having 80% methanol. The soluble portion is purified using ion exchange column chromatography (successively through columns of AG 50, X8 (200 mL, 20-50 mesh, H$^+$ form, Biorad) and then AG 1, X8 (200 mL, 20-50 mesh, OH$^-$ form, Biorad) and eluted with water. The purified floridoside may be further purified by crystallization from hot ethanol.

An alternative method of purifying floridoside includes freezing and grinding alga in liquid nitrogen, extracting with a mixture of methanol, chloroform and water (12:5:3, v/v/v), concentrating the hydroalcoholic phase by evaporation, and purifying the extract using ion exchange column chromatography (successively through columns of AG 50, X8 (200 mL, 20-50 mesh, H$^+$ form, Biorad) and then AG 1, X8 (200 mL, 20-50 mesh, OH$^-$ form, Biorad) and eluted with water. The purified floridoside may be further purified by crystallization from hot ethanol.

The floridoside, the isethionic acid, or both may be administered separately from the antibiotic, or may be admixed with the antibiotic and administered together with the antibiotic. The floridoside and the antibiotic are administered in any manner that maintains the floridoside at a concentration that reduces bacterial efflux pump activity, and that maintains the antibiotic at a concentration that treats the bacterial infection. In some examples, when the floridoside is administered to an animal, such as a human being, it is desirable to maintain the concentration of floridoside at or above about 15 μg of floridoside per mL of body fluid. When administered separately, the floridoside and the antibiotic may be administered at the same time, or may be administered sequentially. In sequential administration, the floridoside may be administered a predetermined amount of time before or after the antibiotic is administered. The predetermined period of time may be, for example: 30 minutes, 1 hour, 2, 3, 4, 5, 6, 7, 8, 9, 10, 11 or 12 hours (or a time between any of the noted times) before or after the antibiotic is administered.

When the floridoside is administered to an animal, such as a human being, the floridoside, the isethionic acid, or both may be formulated for oral, intravenous, topical, or subcutaneous administration. It is not necessary for the floridoside, the isethionic acid, or both to be administered using the same route of administration as the antibiotic. The floridoside, the isethionic acid, or both may be formulated for application to a plant or an animal, such as a human being. The combination therapy comprising floridoside, isethionic acid, or both, in combination with an antibiotic, may be administered to a plant or an animal, such as a human being.

EXAMPLES

Materials.

Nalidixic acid resistant strain of *S. Enteritidis* was provided by Laboratory for Foodborne Zoonoses, Public Health Agency of Canada, Guelph, Ontario. Half strength tryptic soy agar (TSA) medium (Difco) supplemented with nalidixic acid at a concentration of 32 μg/mL was used for bacterial growth. Tetracycline and Streptomycin were obtained from Sigma Aldrich (Oakville, Ontario, Canada). Stock solutions of antibiotics and seaweed extract were prepared and stored at −20° C. Other chemicals and media were purchased from Difco Laboratories, Baltimore, Md., USA. Red seaweeds (*Chondrus crispus*, and *Sarcodiotheca gaudichaudii*) were provided by Acadian Seaplants Limited, Nova Scotia, Canada.

Statistical Analysis

A completely randomized design was followed for all assays. Experiments were performed three times with three biological replicates. Data was analyzed using ANOVA one-way analysis of variance with a P value of 0.05 using the statistical software Minitab and SAS. For significant main effects, the Tukey's procedure was used to compare differences among the least-square means. The standard error of each mean (SEM) was reported with the mean. Differences were considered significant when P was <0.05.

Example 1. Preparation of Seaweed Extract (SWE) and Floridoside

Seaweed water extracts (SWE) were prepared by grinding sun dried seaweeds to fine powder using a coffee grinder, and adding 5 grams of algal powder to 20 mL distilled water (DW). The resulting slurry was incubated at 50° C. for 3 hours under shaking condition at 140 rpm using an orbital shaker (New Brunswick Scientific, Enfield, Conn., US). The slurry was then centrifuged at 10,000 g for 15 min. The supernatant was recovered and the residual pellet was re-extracted three times using the same procedure. The resulting supernatants were pooled and freeze dried (Thermo Fisher Scientific Inc., US). Dilutions of SWE were prepared by dissolving 0.2, 0.4, 0.8, 1 and 2 g of soluble freeze dried extract in 1 mL distilled water. These dilutions were used as working concentration in all the experiments.

Floridoside can be extracted and purified from red seaweed, such as *Chondrus crispus, Gymnogongrus devoniensis, Palmaria palmata Sarcodiotheca gaudichaudii, Solieria chordalis* and *Sarcodiotheca* spp., by following the method described by Christelle Simon-Colin and others in *Phycological Research* (2002) 50: 125-128, which is incorporated herein by reference; or the method described by Veronique Kerjean and others in *Botanica Marina* (2007) 50: 59-64, which is incorporated herein by reference.

Example 2. Determination of Minimum Inhibitory Concentrations (MIC) of Antibiotics The susceptibility of *S. Enteritidis* to tetracycline and streptomycin was tested by broth inoculation method. The testing of MICs ($MIC_{25}$ and $MIC_{50}$) was performed in triplicates with an inoculum of $1 \times 10^8$ cells/mL. MICs were determined as the lowest concentration of antibiotics required for complete inhibition of bacteria after incubation at 37° C. for 16-18 h in an incubator shaking at 200 rpm. MATLAB R2010a (curve fitting tool) was used to determine minimum inhibitory concentrations (MIC) of the antibiotics. For tetracycline, the MIC for 50% of the strains ($MIC_{50}$) was ≤4 μg/mL and 25% of the strains ($MIC_{25}$) was ≤7.9 μg/mL. Streptomycin exhibited higher antimicrobial activity against *S. Enteritidis* compared to tetracycline with $MIC_{25}$ and $MIC_{50}$ 1 μg/mL and 1.63 μg/mL, respectively.

Example 3. Combined Effect of SWE and Antibiotics on *Salmonella Enteritidis*

The combined effect of the *C. crispus* (CC) extract or the *S. gaudichaudii* (SG) extract, with tetracycline or streptomycin (at $MIC_{25}$ or $MIC_{50}$), was evaluated in vitro by liquid culture inhibition test. To 10 mL of tryptic soy broth, seaweed extract (SWE) and 100 µL *Salmonella Enteritidis* (OD600=0.1, 1×10$^8$ cells/mL) were added. The final concentrations of seaweed extracts in 10 mL with tryptic soy broth were 200, 400, or 800 µg/mL. Culture tubes were incubated at 37° C. for 24 hrs. The growth of *S. Enteritidis* was determined by plating the serially diluted culture on TSA plates to enumerate the colony forming units (CFU).

The combination of tetracycline and the CC extract at 400 µg/mL (log CFU 5.4 at MIC$_{50}$, p=0.01, n=9) and 800 µg/mL (log CFU 6.1 at MIC$_{25}$ and 5.8 at MIC$_{50}$, p=0.01, n=9) did not affect the growth of *S. Enteritidis* compared to tetracycline alone (log CFU 6.1 and 5.5 at MIC$_{25}$ and MIC$_{50}$ respectively, p=0.01, n=9). However the combination of tetracycline at MIC$_{25}$ and 400 µg/mL of CC extract was effective in reducing *S. Enteritidis* growth. Moreover, the lowest concentration of CC extract (200 µg/mL) and tetracycline (MIC$_{25}$ and MIC$_{50}$) was the most effective in reducing the bacterial growth (log CFU 4.7 and 4.5 at MIC25 and MIC50 respectively).

For the SG extract, the response was dose dependent, with the higher concentration of SG extract (400 and 800 µg/mL, p=0.05, n=9) in combination with tetracycline showed complete inhibition of bacterial growth. With 200 µg/mL of the SG extract, the bacterial growth was reduced (log CFU 4.8 and 4.5 at MIC$_{25}$ and MIC$_{50}$ respectively), significantly lower than MIC controls (log CFU 5.5).

The antimicrobial effect of SWE (CC and SG) and streptomycin (MIC$_{25}$ and MIC$_{50}$) was similarly tested. Similar trends were observed for streptomycin and both the CC and SG extracts against *S. Enteritidis*. The combination treatment with lowest concentration of CC extract (200 µg/mL) showed log CFU of 4.1 and 4.3 at MIC$_{50}$ and MIC$_{25}$, respectively (p=0.05, n=9) and the highest concentration of SG extract (800 µg/mL) showed log CFU 0 at MIC$_{50}$ and MIC$_{25}$ respectively (p=0.05, n=9). Comparison of inhibitory effect of both antibiotic combinations with SWE, tetracycline showed better combinatory effect and was used in the further experiments. Without wishing to be bound by theory, the authors of the present disclosure believe that tetracycline showed better combinatory effect because tetracycline is more efficiently removed by the bacterial efflux pumps than streptomycin.

The results discussed above are illustrated in FIGS. 1-4. Values with different superscript letters are significantly different (p<0.05). Values represent mean±standard deviation from three independent experiments (n=9).

Example 4. 1H Nuclear Magnetic Resonance Spectroscopy

A 1H nuclear magnetic resonance (1H NMR) spectrum of crude seaweed extracts was obtained using a Bruker Advance DRX200 NMR spectrometer. The NMR analysis identified isethionic acid, citrulline, taurine and floridoside as the four major compounds in the water extracts of CC and SG.

Example 5. Antimicrobial Effect of Seaweed Pure Compounds on *Salmonella Enteritidis*

Pure isethionic acid, citrulline, taurine and floridoside were isolated from seaweeds and identified by 1H NMR/MS. These pure compounds were tested in vitro against *S. Enteritidis* using the broth inoculation method of Example 2, but without the tetracycline or streptomycin. Fifteen (15) µg/mL of each compound was added to TSA broth and inoculated with *S. Enteritidis*. Antimicrobial activity was determined as a measure of log CFU/mL.

Floridoside and isethionic acid both significantly reduced the colony count (log CFU 6.21 and 6.33 respectively, p=0.09, n=9) of *S. Enteritidis* compared to control (log CFU 6.5, p=0.09, n=9). However, no statistically significant difference was observed in CFU of *S. Enteritidis* when treated with citrulline or taurine. Of the two effective compounds (floridoside and isethionic acid), floridoside showed highest activity and was selected for the further experiments.

Figure 5:
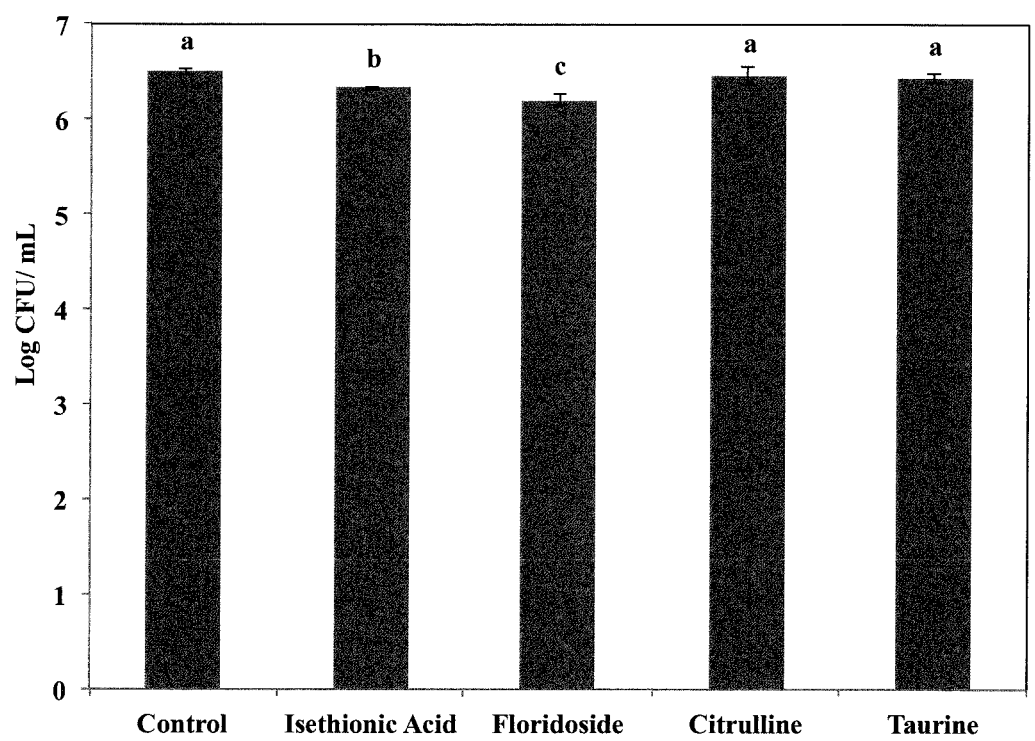
FIG. 5 is a graph illustrating the antimicrobial effect of isethionic acid, citrulline, taurine and floridoside on the growth of *S. Enteritidis*.

These results are illustrated in FIG. 5. Values with different superscript letters are significantly different (p<0.05). Values represent mean±standard deviation from three independent experiments (n=9).

Example 6. Combined Effect of Floridoside and Tetracycline on *Salmonella Enteritidis*

Synergistic interactions of floridoside and tetracycline (MIC$_{25}$ and MIC$_{50}$) were evaluated in vitro by liquid culture inhibition test as described in Example 2. Briefly, the bacterial cells were growth in the presence of floridoside (15 µg/mL)+tetracycline (MIC$_{25}$, 4 µg/mL), or floridoside (15 µg/mL)+(MIC$_{50}$, 7.9 µg/mL). Tetracycline (MIC$_{25}$ and MIC$_{50}$) and floridoside (15 µg/mL) were used as control. Antimicrobial activity was determined as a measure of log CFU/mL.

Floridoside at 15 µg/mL potentiated the activity of tetracycline at both MICs (log CFU 4.3-5.2 (p<0.05, n=9)). Sub lethal concentration of tetracycline (MIC$_{50}$ and MIC$_{25}$; 4 and 7.9 µg/mL respectively) in combination with floridoside (15 µg/mL) exhibited antimicrobial activity comparable to full strength tetracycline (23 µg/mL). Compared to MICs alone, the combination of tetracycline (MIC$_{50}$ and MIC$_{25}$) and 25 µg/mL of floridoside inhibited (log CFU 6.05 and 4.7, p<0.05, n=9) the growth of *S. Enteritidis*. The numbers of bacterial aggregates at higher concentrations of floridoside (50 and 100 µg/mL) in combination with tetracycline were not significantly different than the control (p<0.05, n=9).

Figure 6:
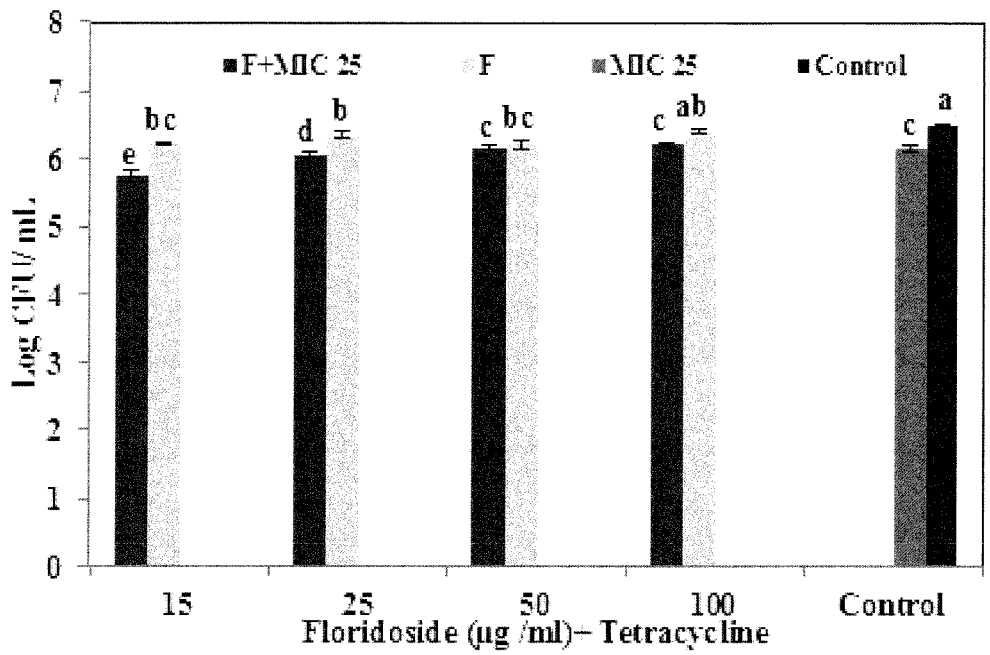
FIG. 6 is graph illustrating the combined effect of floridoside and tetracycline at $MIC_{25}$ on the growth of *S. Enteritidis*.
Figure 7:
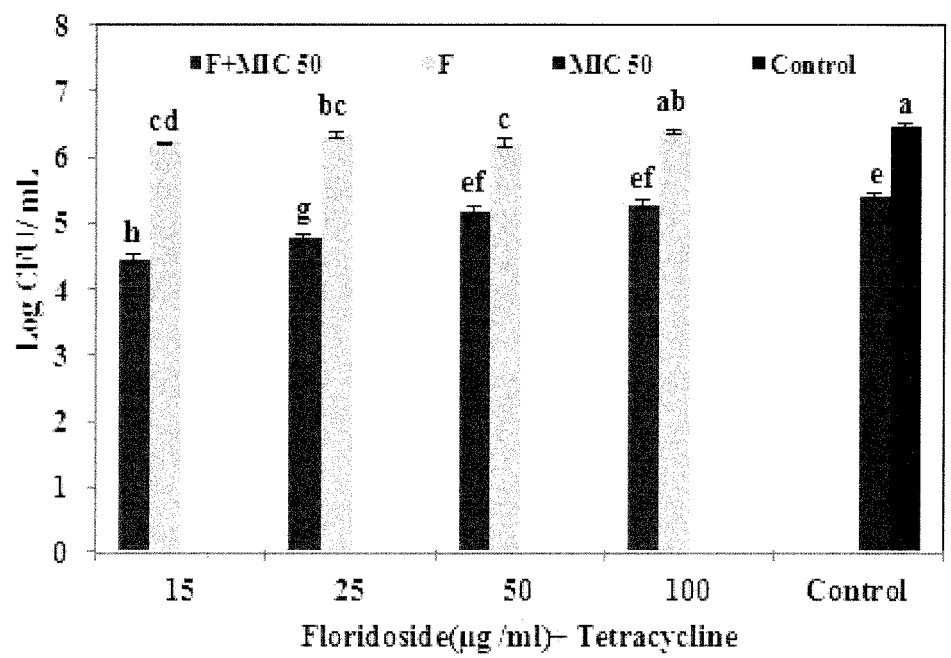
FIG. 7 is graph illustrating the combined effect of floridoside and tetracycline at $MIC_{50}$ on the growth of *S. Enteritidis*.

These results are illustrated in FIG. 6 (MIC$_{25}$) and FIG. 7 (MIC$_{50}$). Values with different superscript letters are significantly different (p<0.05). Values represent mean±standard deviation from three independent experiments (n=9).

Example 7. Effect of Floridoside and Tetracycline on Expression of Efflux Pumps Related Genes Gene expression analysis was carried out at 45, 90 and 180 min to understand the mechanism of combinatorial effect of tetracycline and SWE. For gene expression analysis, *S. Enteritidis* with an initial OD600 of 0.1 was cultured at 37° C. TSB in the presence and absence (control) of floridoside with shaking at 160 rpm. Bacterial cells were harvested by centrifugation at 12000 g for 10 mins. Total RNA was extracted using Trizol (Invitrogen) as described by the manufacturer. The RNA was quantified by NanoDrop ND-2000 spectrophotometer (NanoDrop Technologies Wilmington, Del.) and the quality was assessed by agarose gel electrophoresis.

RNA from each biological replicate was used for cDNA synthesis using the High Capacity cDNA reverse transcription kit (Applied Biosystems). The relative transcript levels of quorum sensing, virulence, and flagella associated genes were quantified using StepOnePlus Real time PCR (Applied Biosystems, ON, Canada). The reaction mix contained 2 ng of cDNA, 5 µL Promega GoTaq SYBR green master mix (Promega North America, Madison, Wis., USA) and 300 nM of each gene specific primer shown in Table 1, below. 16SrRNA and tuf-A genes were used as internal control and the relative expression levels were determined by ΔΔ CT method.

TABLE 1

The efflux pump related genes and primer sequences used in the RT-qPCR of Example 7

| Gene | Primer Sequence (5'→3') |
|------|------------------------|
| ramA | CGTCATGCGGGTATTCCAAGTG (SEQ ID NO: 1)<br>CGCGCCGCCAGTTTTAGC (SEQ ID NO: 2) |
| marA | ATCCGCAGCCGTAAAATGAC (SEQ ID NO: 3)<br>TGGTTCAGCGGCAGCATATA (SEQ ID NO: 4) |
| acrB | TTTTGCAGGGCGCGGTCAGAATAC (SEQ ID NO: 5)<br>TGCGGTGCCCAGCTCAACGAT (SEQ ID NO: 6) |

Figure 8:
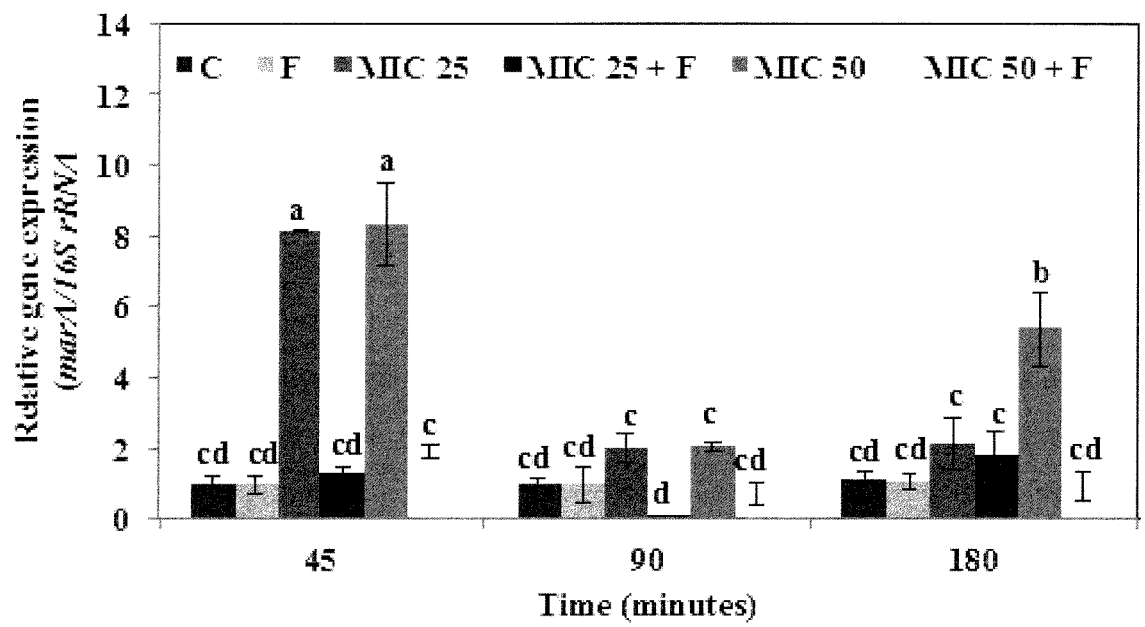
FIG. 8 is a graph showing the relative gene expression of marA after 45, 90, and 180 minutes of treatment with floridoside (15 µg/mL) and tetracycline ($MIC_{25}$ & $MIC_{50}$, 4 and 7.9 µg/mL)
Figure 9:
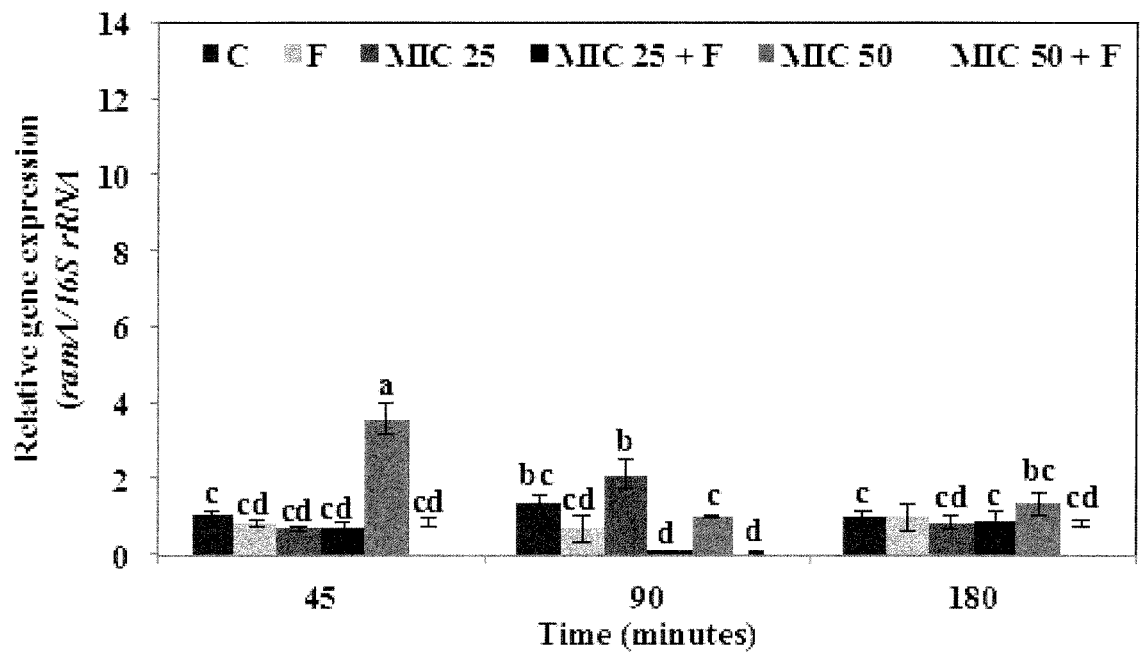
FIG. 9 is a graph showing the relative gene expression of ramA after 45, 90, and 180 minutes of treatment with floridoside (15 µg/mL) and tetracycline ($MIC_{25}$ & $MIC_{50}$, 4 and 7.9 µg/mL)
Figure 10:
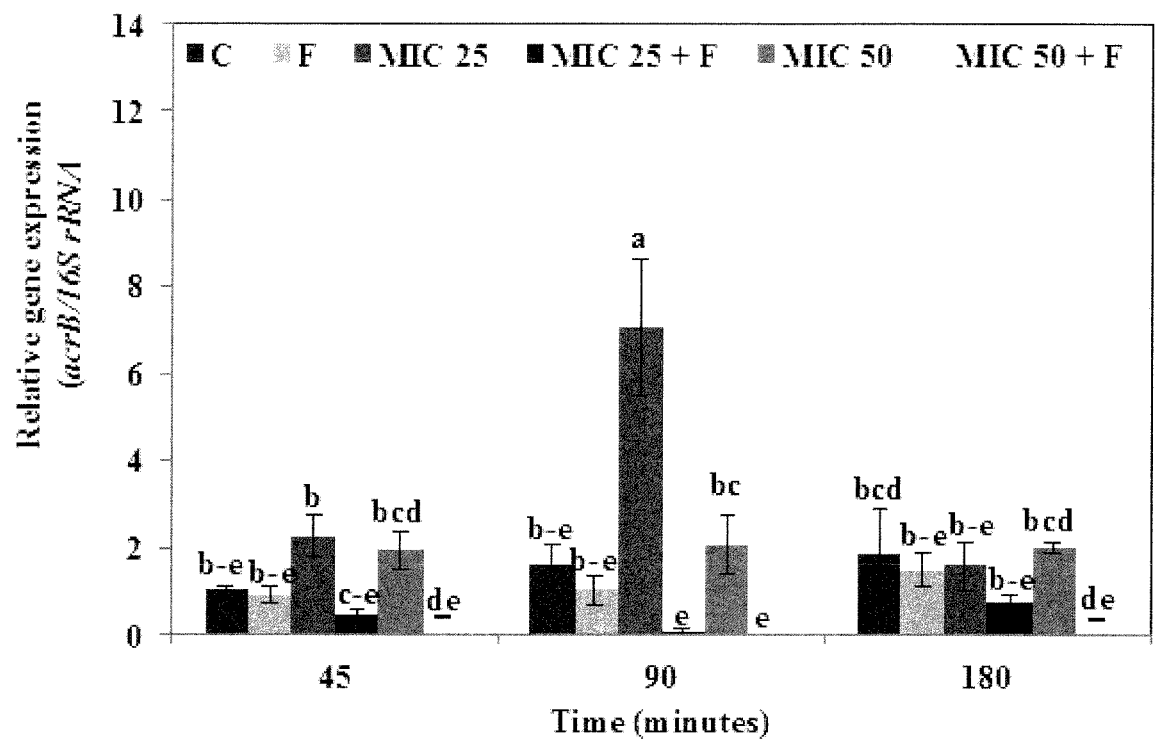
FIG. 10 is a graph showing the relative gene expression of acrB after 45, 90, and 180 minutes of treatment with floridoside (15 µg/mL) and tetracycline ($MIC_{25}$ & $MIC_{50}$, 4 and 7.9 µg/mL)

Real-Time PCR analysis showed that the combination of floridoside and tetracycline ($MIC_{25}$ & $MIC_{50}$) suppressed the expression of efflux related genes after 90 mins of treatment. The relative transcript level of marA, which encodes for global regulator of multidrug efflux pump was repressed by 2-15 fold compared to control MIC treatments (FIG. 8). Similarly, arcB gene encoding the transporter component of the main efflux pump (AcrAB) and ramA, transcriptional activator of protein RamA involved in multidrug efflux pump were down regulated by 18-25 fold and 14-20 folds, respectively ($p<0.001$, $n=9$) (FIGS. 9 and 10). These results suggest that floridoside favours the accumulation of tetracycline in the cell by repressing the expression of efflux pump genes.

FIGS. 8-10 are graphs showing the relative gene expression of marA (FIG. 8), ramA (FIG. 9) and acrB (FIG. 10) after 45, 90, and 180 minutes of treatment with floridoside (15 μg/mL and Tetracycline ($MIC_{25}$ & $MIC_{50}$, 4 and 7.9 μg/mL). Values with different superscript letters are significantly different ($p<0.05$). Values represent Mean±Standard deviation from three independent experiments ($n=9$).

Example 8. Floridoside Potentiates Activity of Antibiotic Against a Wide Range of Bacteria (Gram Positive, Gram Negative, Animal and Human Pathogenic and Non-Pathogenic Forms)

Synergy between tetracycline and floridoside against beneficial and plant pathogenic bacteria was evaluated using 96 well plate by spectrophotometric method. The absorbance was measured at 600 nm. The interaction between floridoside and tetracycline showed synergism in reducing the growth of *Bacillus subtilis* (gram positive, non-pathogenic), *Pseudomonas syringe* DC3000 (plant pathogen), *Pseudomonas* fluorescence (non-pathogenic), and *Pseudomonas putida*. The growth of Pst DC3000 at lower concentration of floridoside (15 μg/ml) in combination with tetracycline ($MIC_{50}$) was significantly reduced (A600=0.013) as compared to control (A600=0.093).

Figure 11:
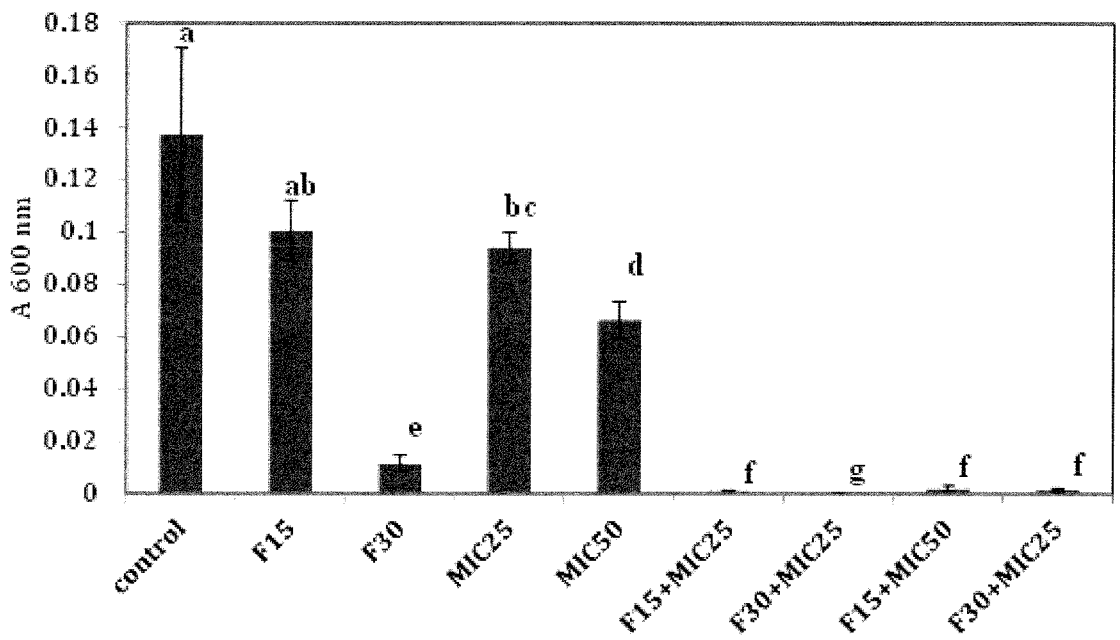
FIG. 11 is a graph showing the results of floridoside at 15 or 30 µg/mL, tetracycline at $MIC_{25}$ or $MIC_{50}$, and combinations thereof, against *Bacillus subtilis*.
Figure 12:
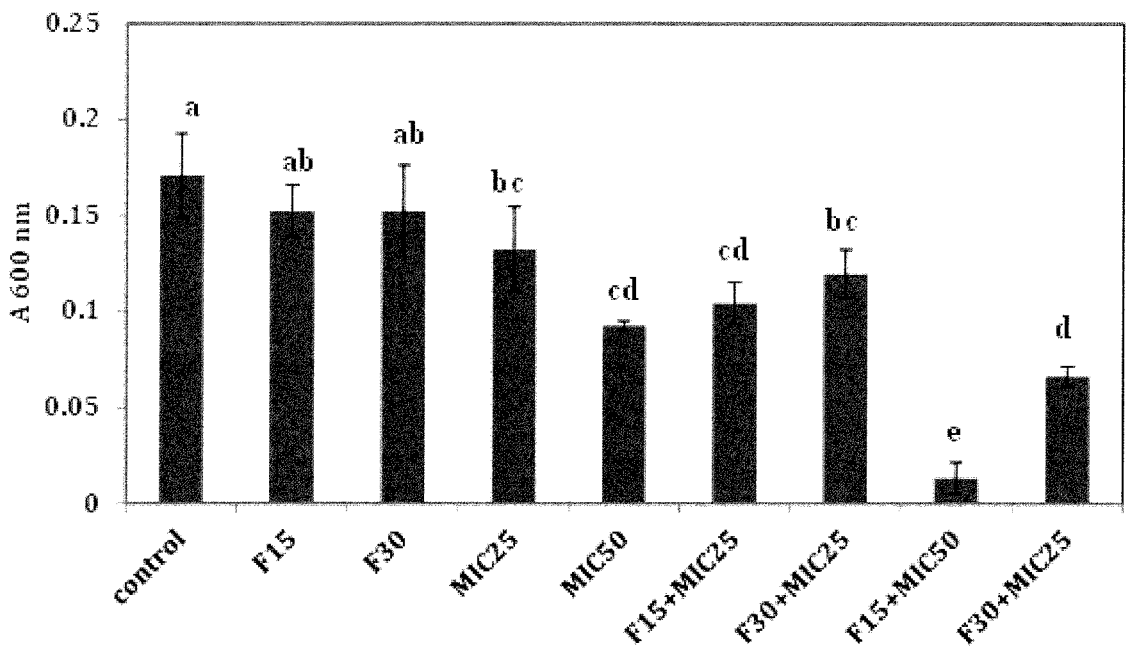
FIG. 12 is a graph showing the results of floridoside at 15 or 30 µg/mL, tetracycline at $MIC_{25}$ or $MIC_{50}$, and combinations thereof, against *Pseudomonas syringe* DC3000.
Figure 13:
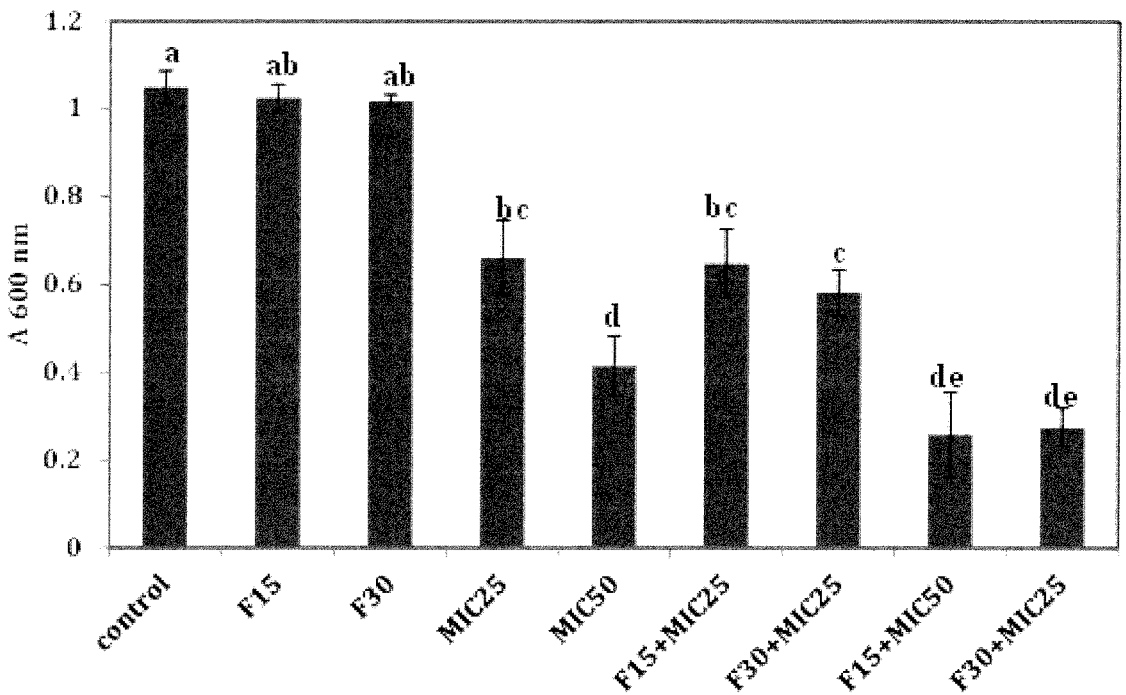
FIG. 13 is a graph showing the results of floridoside at 15 or 30 µg/mL, tetracycline at $MIC_{25}$ or $MIC_{50}$, and combinations thereof, against *Pseudomonas fluorescence*.
Figure 14:
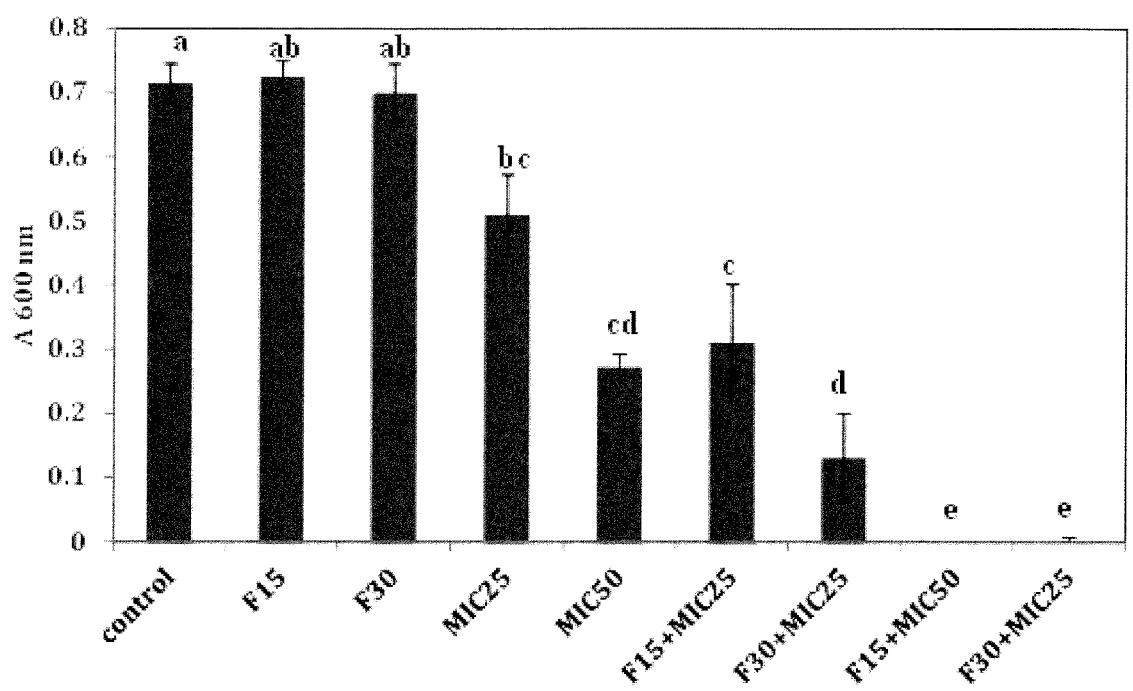
FIG. 14 is a graph showing the results of floridoside at 15 or 30 µg/mL, tetracycline at $MIC_{25}$ or $MIC_{50}$, and combinations thereof, against *Pseudomonas putida*.

These results are illustrated in FIGS. 11-14, which show the results of floridoside at 15 or 30 μg/mL, tetracycline at $MIC_{25}$ or $MIC_{50}$, and combinations thereof. FIG. 11 illustrates the results against *Bacillus subtilis*. FIG. 12 illustrates the results against *Pseudomonas syringe* DC3000. FIG. 13 illustrates the results against *Pseudomonas* fluorescence. FIG. 14 illustrates the results against *Pseudomonas putida*. Values with different superscript letters are significantly different ($p<0.05$). Values represent mean±standard deviation from three independent experiments ($n=24$).

In the preceding description, for purposes of explanation, numerous details are set forth in order to provide a thorough understanding of the examples. However, it will be apparent to one skilled in the art that these specific details are not required. Accordingly, what has been described is merely illustrative of the application of the described examples and numerous modifications and variations are possible in light of the above teachings.

Since the above description provides examples, it will be appreciated that modifications and variations can be effected to the particular examples by those of skill in the art. Accordingly, the scope of the claims should not be limited by the particular examples set forth herein, but should be construed in a manner consistent with the specification as a whole.

What is claimed is:

1. A combination comprising: (a) floridoside and (b) tetracycline or streptomycin, for use in the treatment of infectious disease caused by bacteria in a human, an animal or a plant.

2. The combination of claim 1, wherein the floridoside is formulated for administration together with the tetracycline or streptomycin.

3. The combination of claim 1, wherein the floridoside is formulated for administration separately from the tetracycline or streptomycin.

4. The combination of claim 3, wherein the floridoside is formulated for sequential administration with the tetracycline or streptomycin.

5. The combination of claim 1, wherein the combination comprises floridoside and tetracycline.

6. The combination of claim 1, wherein the floridoside is formulated for oral, intravenous, topical, or subcutaneous administration.

7. The combination of claim 1, wherein the combination comprises floridoside and streptomycin.

8. A method of potentiating the antibiotic activity of tetracycline or streptomycin administered to an animal or a plant, the method comprising: administering floridoside or isethionic acid to the animal or the plant.

9. The method according to claim 8, wherein the floridoside or isethionic acid is administered to the animal or the plant together with the tetracycline or streptomycin.

10. The method according to claim 8, wherein the floridoside isethionic acid is administered to the animal or the plant separately from the tetracycline or streptomycin.

11. The method according to claim 10, wherein the floridoside or isethionic acid is administered to the animal or the plant a predetermined period of time before the tetracycline or streptomycin is administered to the animal or the plant.

12. The method according to claim 10, wherein the floridoside or isethionic acid is administered to the animal or the plant a predetermined period of time after the tetracycline or streptomycin is administered to the animal or the plant.

13. The method according to claim 8, wherein the floridoside or the isethionic acid is administered to the animal via oral, intravenous, topical, or subcutaneous administration.

14. The method according to claim 8, wherein the method comprises administering floridoside.

15. The method according to claim 8, wherein the method comprises administering isethionic acid.

16. The method of claim 8, wherein tetracycline is administered to the animal or the plant.

17. The method of claim 8, wherein streptomycin is administered to the animal or the plant.

* * * * *